(12) United States Patent
Chen et al.

(10) Patent No.: US 9,451,781 B2
(45) Date of Patent: Sep. 27, 2016

(54) STRAIN OF CADMIUM-REMOVING LACTOBACILLUS PLANTARUM BACTERIUM, AND USES OF THE SAME

(71) Applicant: Jiangnan University, Wuxi (CN)

(72) Inventors: Wei Chen, Wuxi (CN); Fengwei Tian, Wuxi (CN); Qixiao Zhai, Wuxi (CN); Gang Wang, Wuxi (CN); Xiaoming Liu, Wuxi (CN); Qiuxiang Zhang, Wuxi (CN); Daming Fan, Wuxi (CN); Jianxin Zhao, Wuxi (CN); Hao Zhang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 150 days.

(21) Appl. No.: 14/241,082

(22) PCT Filed: Dec. 7, 2012

(86) PCT No.: PCT/CN2012/086139
§ 371 (c)(1),
(2) Date: Feb. 26, 2014

(87) PCT Pub. No.: WO2014/032375
PCT Pub. Date: Mar. 6, 2014

(65) Prior Publication Data
US 2014/0341873 A1   Nov. 20, 2014

(30) Foreign Application Priority Data

Sep. 3, 2012 (CN) .............................. 2012 1 033124

(51) Int. Cl.
| | |
|---|---|
| *C12N 1/20* | (2006.01) |
| *A23C 9/123* | (2006.01) |
| *C12R 1/25* | (2006.01) |
| *A23C 13/16* | (2006.01) |
| *A23L 1/212* | (2006.01) |
| *A61K 35/742* | (2015.01) |
| *A23C 11/10* | (2006.01) |
| *A23C 19/032* | (2006.01) |
| *A23L 1/30* | (2006.01) |
| *A23L 2/02* | (2006.01) |
| *A23L 2/38* | (2006.01) |
| *A61K 35/747* | (2015.01) |
| *A23L 1/015* | (2006.01) |
| *A61K 35/00* | (2006.01) |

(52) U.S. Cl.
CPC ........... *A23C 9/1234* (2013.01); *A23C 11/106* (2013.01); *A23C 13/16* (2013.01); *A23C 19/0323* (2013.01); *A23L 1/0158* (2013.01); *A23L 1/212* (2013.01); *A23L 1/3014* (2013.01); *A23L 2/02* (2013.01); *A23L 2/382* (2013.01); *A61K 35/742* (2013.01); *A61K 35/747* (2013.01); *C12N 1/20* (2013.01); *C12R 1/25* (2013.01); *A23V 2002/00* (2013.01); *A23Y 2220/67* (2013.01); *A61K 2035/11* (2013.01)

(58) Field of Classification Search
None
See application file for complete search history.

(56) References Cited

U.S. PATENT DOCUMENTS 6,159,465 A * 12/2000 Adlerberth ........... A61K 35/747
424/93.45

FOREIGN PATENT DOCUMENTS

| CN | 102586148 A1 | 7/2012 |
| CN | 102296046 A1 | 12/2012 |

OTHER PUBLICATIONS

Kearney et al., Applied and Environmental Microbiology, Oct. 1990, vol. 56, No. 10, p. 3112-3116.*
Deng X, Yi XE, and Liu G Cadmium removal from aqueous solution by gene-modified *Escherichia coli* JM109. Journal of Hazardous Materials. 2007, 139(2):340-4.
Zhiqi Hao, Heinz R. Reiske, and David B. Wilson Characterization of Cadmium Uptake in Lactobacillus plantarum and Isolation of Cadmium and Manganese Uptake Mutants. Applied and Environmental Microbiology. 1999, 65(11):4741-4745.

* cited by examiner

*Primary Examiner* — Irene Marx
(74) *Attorney, Agent, or Firm* — Lili Chen (57) ABSTRACT

The invention provides a novel strain of cadmium-removing *Lactobacillus plantarum* bacterium, CCFM8610, which has a good tolerance to acidic environments. *Lactobacillus plantarum* CCFM8610 has a good tolerance to cadmium-containing medium and can effectively bind cadmium in vitro. Animal studies have shown that it can effectively reduce tissue cadmium accumulation and facilitate fecal cadmium excretion. *Lactobacillus plantarum* CCFM8610 has a great potential to be used as an active ingredient in cadmium-removing pharmaceutical drugs and fermented foods.

11 Claims, 6 Drawing Sheets

STRAIN OF CADMIUM-REMOVING *LACTOBACILLUS PLANTARUM* BACTERIUM, AND USES OF THE SAME

CROSS-REFERENCES AND RELATED APPLICATIONS

This application is a Section 371 National Stage Application of International Application No. PCT/CN2012/086139, filed Dec. 7, 2012, which claims priority to Chinese Application No. 201210322124.2, entitled "A New Strain of Cadmium-removing *Lactobacillus plantarum* Bacterium, and Uses of the Same", filed Sep. 3, 2012, contents of which are hereby incorporated by reference in their entirety.

BACKGROUND OF THE INVENTION

1. Field of the Invention

The present invention relates to the field of microbiological technologies, and more particularly, relates to a cadmium-removing bacterium *Lactobacillus plantarum* strain and the use of the same.

2. Description of the Related Art

Cadmium is a heavy metal that is extremely harmful to human health, which is very stable in the environment and easy to be accumulated in the body. Metal cadmium can react with oxygen, chlorine, sulfur and other elements to form inorganic compounds and exist in nature in the form of compounds. Most cadmium salts are soluble in water. Nowadays, cadmium is widely used in electroplating, cadmium-nickel batteries, alloys, pigments and plastics, etc. With the increase of its applications in industry and human daily life, cadmium content in water and soil is increased every year. As a result, cadmium has been accumulated in plants and animals (e.g. cadmium contaminated rice, tobacco, sea food, and animal organs), and eventually became accumulated in human beings through the food chain. Cadmium contamination is particularly serious in some Asian countries. In 1995, the outbreak of "Itai-Itai" disease in Japan, which shocked the world, was caused by cadmium contamination in Jinzu River, resulting in highly contaminated rice that were consumed by local residents. In China, cadmium has become one of the most serious environmental pollutants to land and water with the discharge of about 680 tons of cadmium-containing industrial waste every year. It has been reported that the area of arable lands contaminated by cadmium has reached 8000 acres in China and the cadmium content in the rice fields even reaches 25 times more than that of the allowable national limits in some heavily contaminated areas. In 2002, the Ministry of Agriculture conducted a national wide inspection of the rice market and found that 10% of the rice on the market contains levels of cadmium more than that of the national standard. In 2007, professor Gengxing Pan from Nanjing Agriculture University and his research team conducted another inspection of the rice cadmium content in six districts of the country (district of Eastern China, Northeast China, Central China, Southwest China, South China, and North China), and found similar results. Cadmium is highly toxic and has a long incubation period. The Agency for Toxic Substances and Disease Registry (ATSDR) and the United States Environmental Protection Agency (EPA) have been listing Cadmium as the sixth most toxic substance to human health that can cause damage to bone, kidney, liver, respiratory system, circulation system, and reproductive organs. In addition, cadmium can cause cancer. The International Union Against Cancer listed cadmium as an IA level carcinogen in 1993.

Acute cadmium poisoning causes coughing, stuffiness, dyspnea, nausea, vomiting, abdominal pain and other symptoms. Large doses of cadmium intake can even result in death due to acute liver damage. Chronic cadmium poisoning can lead to kidney damage (e.g. proteinuria, kidney stones, and chronic renal failure), bone damage (e.g. bone pain, osteoporosis, osteomalacia, and spontaneous fractures), damage to the reproductive organs (e.g. testes and ovaries damage) and cancer (e.g. lung cancer and prostate cancer). Half-life of cadmium in human body is as long as 10-30 years, which makes cadmium poisoning easily overlooked.

The most common way to treat the physiological disorders caused by cadmium poisoning is to promote cadmium excretion by chelation (e.g. $EDTANa_2Ca$, Sodium dimeraptosuccinate (DMSA)) therapies. For example, Chinese Pharmacopoeia, Second Edition (2000) documented using edetate calcium disodium as antidote for heavy metals poisoning caused by cadmium and lead. However, all of these drugs have side effects to some degree. $EDTANa_2Ca$ is a broad spectrum chelator with a strong renal toxicity. A large number of essential trace elements such as zinc, copper, manganese and iron, which are important for enzyme activities, will be excreted out of human body through urine when using $EDTANa_2Ca$ as a chelator. Therefore extensive uses of calcium disodium edetate can cause damages to human health. DMSA is effective only if given within a short period of time after cadmium exposure and can cause headache, nausea, limb pain and digestive system disorders (Kojima, S., Sugimura, et. al. Effects of dithiocarbamates on testicular toxicity in rats caused by acute exposure to cadmium. Toxicology and applied pharmacology, 116, 24-29, 1992).

Because of some side effects of traditional treatments against cadmium poisoning, there is a need in looking for new intervention or therapeutic methods. Lactic acid bacteria (LAB) is a general name for bacteria that can convert carbohydrates to lactic acid. LAB widely exist in natural fermented dairy products, fermented vegetable foods such as pickles, sauerkraut, silage, and human intestine. Long term studies have showed that some LAB strains are beneficial probiotics that play important roles in human health, for example, preventing lactose intolerance, adjusting the microecological balance, preventing cancer, controlling toxin levels in body, protecting the liver and enhancing its detoxification capability. Furthermore, it has been reported that as a food grade microorganism, LAB can bind and remove heavy metals such as cadmium and lead in vitro (Halttunen, T., Collado, M. C., et. al. Combining strains of lactic acid bacteria may reduce their toxin and heavy metal removal efficiency from aqueous solution. Letters in Applied Microbiology, 46, 160-165, 2007). Therefore, LAB have a great potential to become new healthy foods with cadmium-removing capability.

Currently, a number of patent documents have disclosed methods for preparing healthy foods against cadmium poisoning. Chinese patent CN1336208 discloses a healthy food made of deodorized garlic powder, vinegar powder and "Bing Ming powder" (a mixture of borneol powder and alum powder), which can help excrete cadmium accumulated in human body due to exposure to contaminated air, water, or pesticides. Chinese patent CN1328845 discloses one Chinese medicine made of smilax, red ginseng, panax and some other materials that can effectively function to prevent and treat cadmium poisoning without side effects. However, there are few patents related to cadmium-removing bacteria. Chinese patent CN101153272 discloses that

*Burkholderia yabunchi* J62 has a good tolerance to cadmium and it can be used in the field of environmental engineering to promote plant growth, help plants accumulating cadmium and improve soil quality. Chinese patent CN101252943A discloses a *Lactobacillus plantarum* that can help mammal to absorb iron, zinc, calcium and magnesium ions.

In summary, there is a need in isolating LAB strains having good cadmium tolerance and absorption capacity, proving their cadmium-removing ability in animal models, and developing cadmium-removing LAB products. It is the goal of the present invention to explore novel beneficial features of probiotics, isolate lactic acid bacteria with high health values, and develop a new dietary therapeutic strategy against cadmium poisoning.

SUMMARY OF THE INVENTION

One goal of the present invention is to provide a cadmium-removing bacterium, *Lactobacillus plantarum* CCFM8610. The other goal of the present invention is to provide applications of *Lactobacillus plantarum* CCFM8610.

1. *Lactobacillus plantarum* CCFM8610

The present invention relates to a lactic acid bacterium strain, which is identified as a *Lactobacillus plantarum* (CCFM8610) strain based on the morphological, physiological and biochemical traits of the strain. The *Lactobacillus plantarum* CCFM8610 was deposited in China General Microbiological Culture Collection Center (CGMCC), Institute of Microbiology of Chinese Academy of Science, NO. 1 Beichen West Road, Chaoyang District, Beijing, on May 3, 2012, with the accession number CGMCC No. 6077.

*Lactobacillus plantarum* CCFM8610 has the following characteristics:

(1) good acid tolerance with the ability to grow well under pH 3.0 to 9.0 and can survive under pH 2.5;

(2) good tolerance to cadmium when cultured in a culture medium containing cadmium;

(3) good cadmium absorption capacity when incubated in an aqueous solution containing cadmium;

(4) ability to effectively decrease tissue cadmium accumulation and facilitate fecal excretion of cadmium in cadmium-exposed mice.

2. Application of *Lactobacillus plantarum* CCFM8610 in developing drugs and foods against cadmium toxicity.

In one embodiment, the present invention provides cadmium-removing drugs or fermented foods comprising viable *Lactobacillus plantarum* CCFM8610.

In another embodiment, the present invention provides cadmium-removing drugs comprising viable *Lactobacillus plantarum* CCFM8610 and pharmaceutically acceptable drug carriers.

In another embodiment of the present invention, the viable *Lactobacillus plantarum* CCFM8610 is prepared as a powder using conventional freeze-drying or other preparation methods. The resulting powder contains $10^6$ CFU viable *Lactobacillus plantarum* CCFM8610 cells per gram.

In another embodiment of the present invention, the drug carrier(s) can be one or more carriers selected from pharmaceutical grade fillers, adhesives, wetting agents, disintegrants, lubricants and flavoring agents.

The cadmium-removing drugs can be granules, capsules, tablets, pills or oral liquid.

In another embodiment, the present invention provides cadmium-removing fermentated foods, which can be dairy products, soy bean products, fruit products or vegetable products prepared by fermentation with *Lactobacillus plantarum* CCFM8610.

The *Lactobacillus plantarum* CCFM8610 used for fermentation is prepared as follows:

A, Preparation of culture medium. The ingredients are (w/w, %): $H_2O$ 87.7, skim milk (enzymatic hydrolysis milk) 10, glucose 0.5, tryptone 1.5, yeast extract 0.3, pH 6.8. Mix all the ingredients as described above and adjust pH to be 6.8. The percentage is calculated based on total weight.

B, Preparation of protective agent. The ingredients are 100 g/L skim milk, 30 mL/L glycerol, 100 g/L maltodextrin, 150 g/L trehalose, and 10 g/L L-glutamate. Dissolve the ingredients above into water to make a protective agent.

C, *Lactobacillus plantarum* CCFM8610 is inoculated at a 2-4% (w/w) ratio into a sterile culture medium (sterilized under 110-120° C. for 8 to 12 minutes) and cultured at 37° C. for 18 hours. The bacteria cells are washed 2-4 times with phosphate buffer (pH 7.2) and then suspended in the protective agent to a concentration of $10^{10}$ CFU/mL. The suspension is then incubated at 37° C. for 60 minutes before subject to a conventional freeze-drying procedure. The freeze-dried *Lactobacillus plantarum* CCFM8610 powder is used as the starter culture.

In some embodiment of the present invention, the cadmium-removing dairy products can be dairy products, sour cream or cheese containing *Lactobacillus plantarum* CCFM8610 powder.

In some embodiment of the present invention, the cadmium-removing soy bean products can be soy milk, lobster sauce or soybean paste containing *Lactobacillus plantarum* CCFM8610 powder.

In some embodiment of the present invention, the cadmium-removing fruit products and vegetable products can be cucumbers, carrots, beets, celeries or cabbage products containing *Lactobacillus plantarum* CCFM8610 powder.

DETAILED DESCRIPTION

1. *Lactobacillus plantarum* CCFM8610

The present invention relates to a lactic acid bacterium strain, *Lactobacillus plantarum* CCFM8610, which was deposited in China General Microbiological Culture Collection Center (CGMCC), Institute of Microbiology of Chinese Academy of Science, NO. 1 Beichen West Road, Chaoyang District, Beijing, on May 3, 2012, with the accession number CGMCC No. 6077.

Based on the selection criteria below, a large number of experiments and technical analyses have been conducted to isolate *Lactobacillus plantarum* CCFM8610 from traditional Chinese foods such as pickles and fermented milk wine, which possesses the following characteristics:

(1) good acid tolerance with the ability to grow well under pH 3.0 to 9.0 and can survive under pH 2.5;

(2) good tolerance to cadmium when cultured in a culture medium containing cadmium;

(3) good cadmium binding capacity when incubated in an aqueous solution containing cadmium;

(4) ability to effectively decrease tissue cadmium accumulation and facilitate fecal excretion of cadmium in cadmium-exposed mice.

The experimental results and technical analyses on *Lactobacillus plantarum* CCFM8610 are described below in more details.

(1) *Lactobacillus plantarum* CCFM8610 has a good acid tolerance with the ability to grow under pH 3.0-9.0 and survive under pH 2.5.

The cryopreserved *Lactobacillus plantarum* CCFM8610 was cultured in MRS medium (Qingdao Hope Bio-Technology Co., Ltd, Qingdao, Shandong, China) at 37° C. for 24 hours. The bacterial culture was then subcultured in MRS medium for 2-3 times. Next, 1 mL of *Lactobacillus plantarum* CCFM8610 culture was inoculated into 19 mL MRS medium with pH values from 3.0 to 9.0 and cultured at 37° C. for 24 hours. Measure the $OD_{600}$ before and after the culture of the strain and use the $OD_{600}$ value to determine the concentration of cells in the culture medium and evaluate how well cells grow under a particular pH value. $OD_{600}$ is the absorbance of the liquid culture medium measured at the wavelength of 600 nm using a spectrophotometer. It is usually used to determine the cell concentration in the liquid culture medium and estimate the cell growth.

The experimental results showed that *Lactobacillus plantarum* CCFM8610 was able to grow well under pH 3.0-9.0. Therefore, further experiments had been performed with *Lactobacillus plantarum* CCFM8610. *Lactobacillus plantarum* CCFM8610 was cultured by the same way mentioned above. The cells were collected and washed twice with phosphate buffer (pH 7.2). The cells were then suspended in 1.0 mL phosphate buffer (pH 7.2) and added to 9.0 mL artificial gastric juice (pH 2.5). The mixture was incubated at 37° C. and cell samples were collected at the beginning (0 hours) and 3 hours of the incubation. The cell samples were cultured in MRS agar plates and counted by standard plate count method. The survival rate (%) is the percentage of logarithm value of viable microorganisms at 3 hours to that of viable microorganisms at 0 hours. Strains having survival rate higher than 80% at pH 2.5 are selected for further research. The survival rate of *Lactobacillus plantarum* CCFM8610 in artificial gastric juice (pH 2.5) is higher than 90%, which means *Lactobacillus plantarum* CCFM8610 is able to survive under pH 2.5.

(2) *Lactobacillus plantarum* CCFM8610 has a good cadmium tolerance when cultured in vitro in a medium containing cadmium.

To determine the cadmium tolerance capacity of *Lactobacillus plantarum* CCFM8610, the strain was cultured in a medium containing different concentrations of cadmium ions. Under sterile conditions, 0.3423 g of $3CdSO_4.8H_2O$ was added to 1 liter water to make an aqueous solution with 150 mg/L cadmium. The aqueous cadmium solution (150 mg/L) was used to dissolve dry MRS medium powder to make a liquid MRS medium with 150 mg/L cadmium ions. The same method can be used to make liquid MRS media with 50 mg/L and 500 mg/L cadmium.

Figure 1:
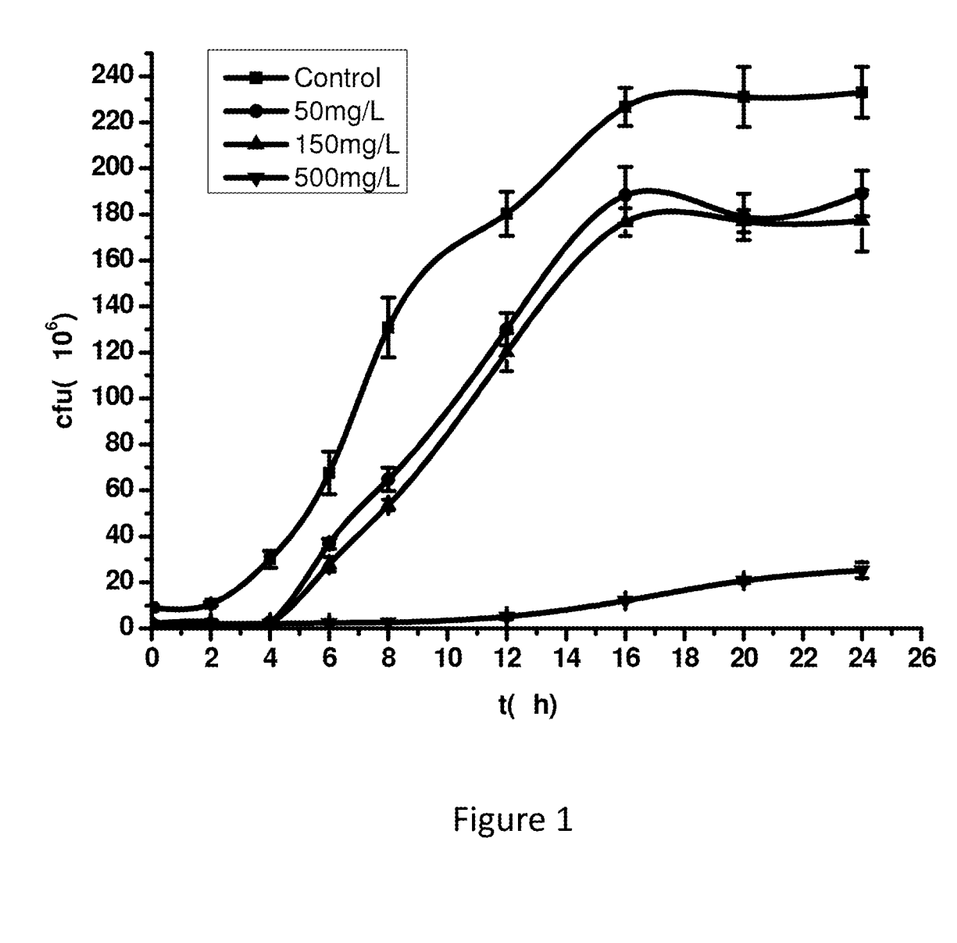
FIG. 1. Cell growth curve of *Lactobacillus plantarum* CCFM8610 in the culture medium containing 50 mg/L, 150 mg/L and 500 mg/L (Initial concentration) cadmium.

*Lactobacillus plantarum* CCFM8610 that entered stationary phase were inoculated at a 2% (w/w) ratio into the cadmium-containing media above. Cell growth was determined by standard plate count at 0, 2, 4, 6, 8, 12, 16, 20, and 24 hours after the start of the culture. The cell growth curve of *Lactobacillus plantarum* CCFM8610 is shown in FIG. 1. As shown in FIG. 1, *Lactobacillus plantarum* CCFM8610 of the invention has a good cadmium tolerance.

(3) *Lactobacillus plantarum* CCFM8610 has a good cadmium absorption capacity when incubated in an aqueous solution containing cadmium.

Figure 2:
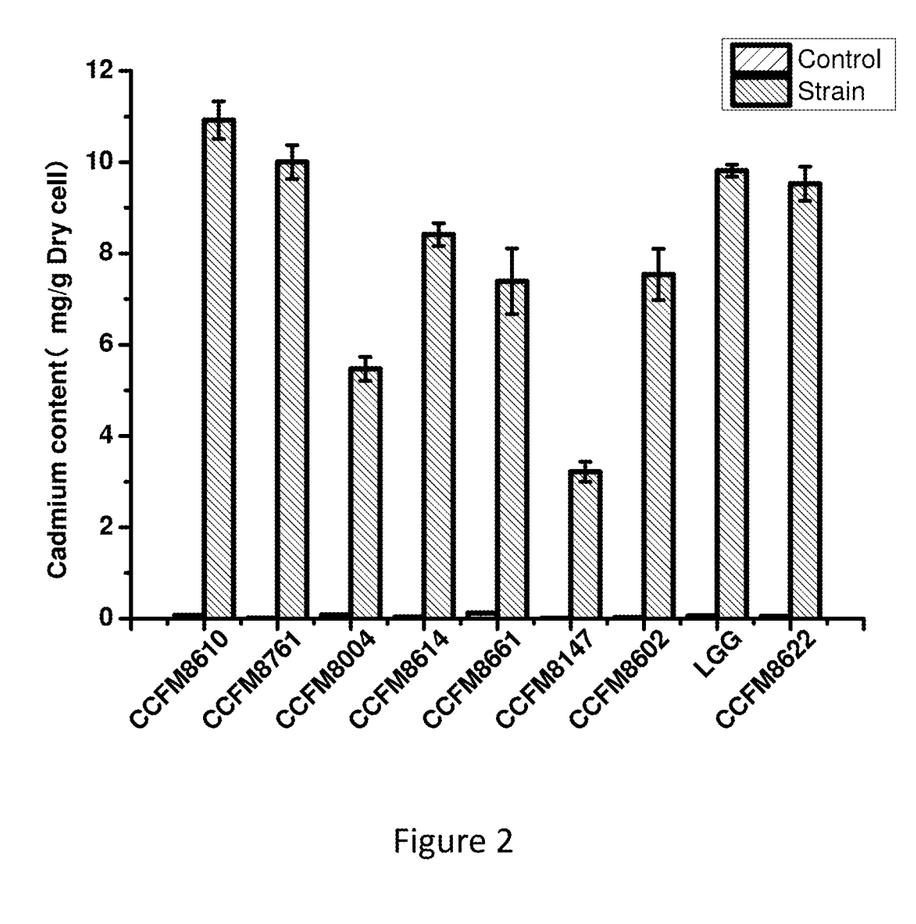
FIG. 2. Cadmium binding abilities of nine lactic acid bacteria strains. CCFM8610, CCFM8614 and CCFM8661 are *Lactobacillus plantarum*. CCFM8761 is *Lactobacillus reuteri*. CCFM8004 is—*Lactobacillus bulgaricus*. CCFM8602 is—*Lactobacillus gasseri*. LGG is *Lactobacillus rhamnosus* GG. CCFM8622 is *Bifidobacterium bifidum*. CCFM8147 is *Lactobacillus delbrueckii*.

Under sterile conditions, nine lactic acid bacteria strains were isolated from the traditional Chinese foods (e.g. pickles and fermented milk wine) based on the acid tolerance selection criterion (e.g. able to grow under pH 3.0). The nine strains were purified and activated and cultured under standard culture condition. The activated cell was transferred to a culture medium containing 150 mg/L cadmium ions with a final bacterial concentration of 1 g/L. The cells were incubated at 37° C. for 1 hour. The cells were centrifuged at 6000 r/min for 20 min, washed with sterile water, and centrifuged again. After the centrifugation, cell pellets were collected and digested in concentrated $HNO_3$, and further digested in a microwave digestion oven for 20 minutes. The cadmium concentration of the digested solution was measured by atomic absorption spectrum analyzer (Spectr AA 220, Varian, USA). The cadmium binding capacity of different strains is shown in FIG. 2. As shown in FIG. 2, comparing to other strains, *Lactobacillus plantarum* CCFM8610 of the invention has the highest biosorption level to cadmium, and therefore it has a strong cadmium ion binding capacity.

(4) *Lactobacillus plantarum* CCFM8610 can effectively decrease tissue cadmium accumulation and facilitate fecal cadmium excretion in cadmium-exposed mice.

60 healthy adult male mice (weight: 20-25 g) were randomly divided into 3 groups, each with 20 mice: a negative control group (no cadmium or CCFM8610), a cadmium-only group and a cadmium plus CCFM8610 (therapy group) group. At the first day of the animal experiment, the mice in the negative control group were administered 0.5 mL plain water via gavage, the mice in other two groups were both administered 0.5 mL 3.6 mg/L $CdSO_4$ solution via gavage. At 1 hour after cadmium exposure, the control and cadmium-only group were administered 0.5 mL skim milk, while the therapy group was administered 0.5 mL skim milk with $2.0 \times 10^9$ CFU/mL *Lactobacillus plantarum* CCFM8610 (made in Example 3) via gavage. At 4, 8, 12, 24 and 48 hours after cadmium exposure, fecal samples of each surviving mouse were collected and digested for cadmium determination. The results were shown in FIG. 4. At 48 hours after cadmium exposure, all mice were sacrificed. Livers and kidneys were excised, cleaned and digested for cadmium estimation. The results were shown in FIG. 3.

Figure 3:
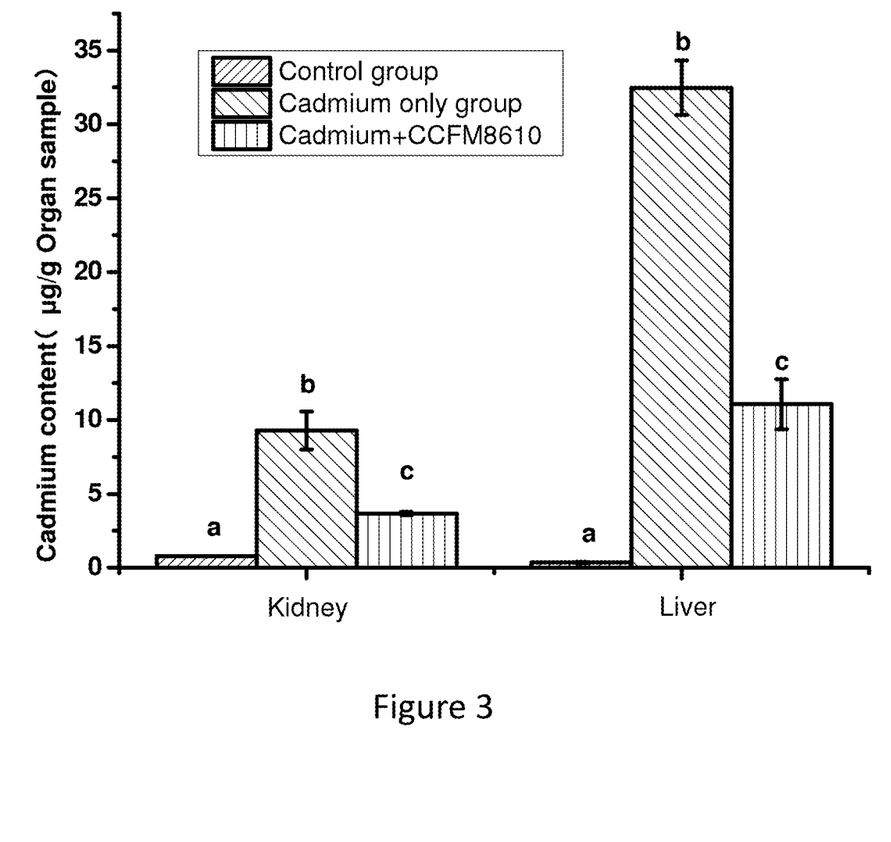
FIG. 3. Effects of CCFM8610 treatment on levels of cadmium in the livers and kidneys of mice. The letters a, b and c mean that cadmium contents in tissues and groups with different letters differ significantly (P<0.05) from each other.
Figure 4:
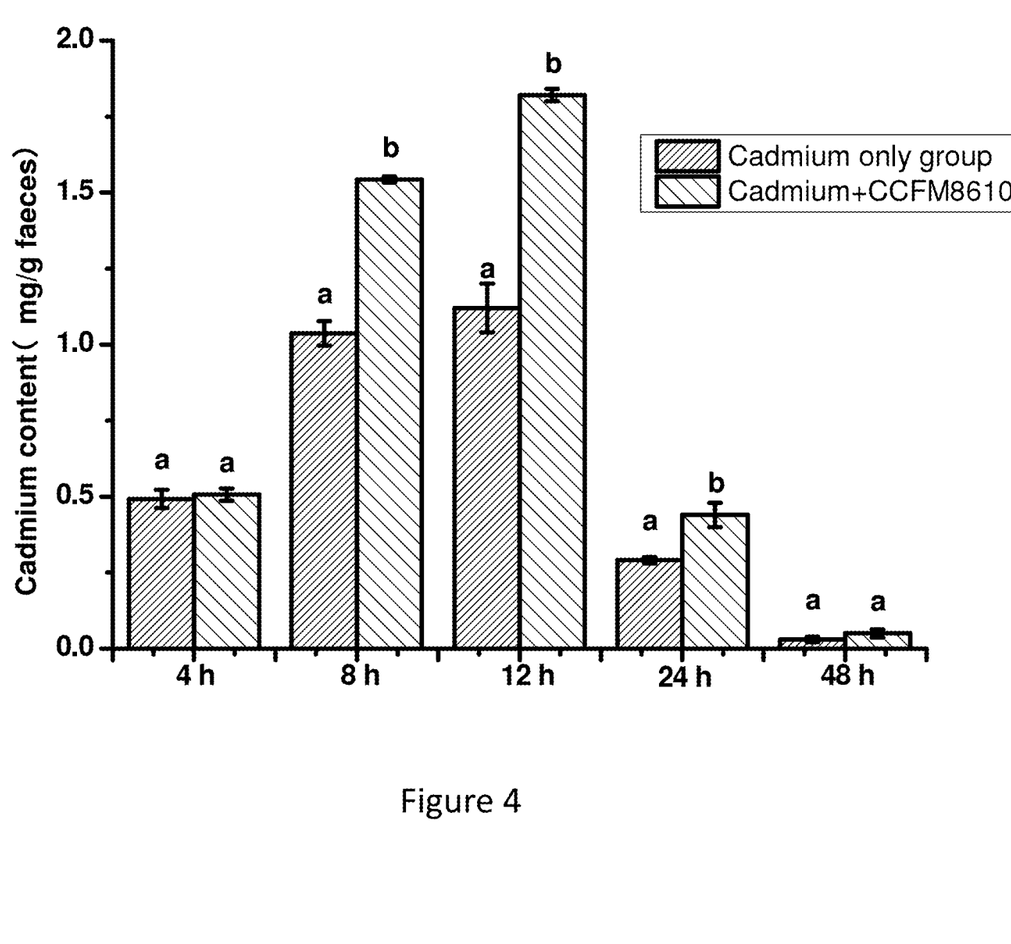
FIG. 4. Effects of CCFM8610 treatments on levels of cadmium in the feces of cadmium-exposed mice. The letters a, b and c mean that in each period, groups with different letters differ significantly (P<0.05).

By comparing the cadmium content in livers, kidneys, and feces of mice in cadmium-only group and the therapy group with *Lactobacillus plantarum* CCFM8610, it is shown that *Lactobacillus plantarum* CCFM8610 treatment can effectively decrease cadmium accumulation in livers and kidneys and facilitate fecal cadmium excretion.

Figure 5:
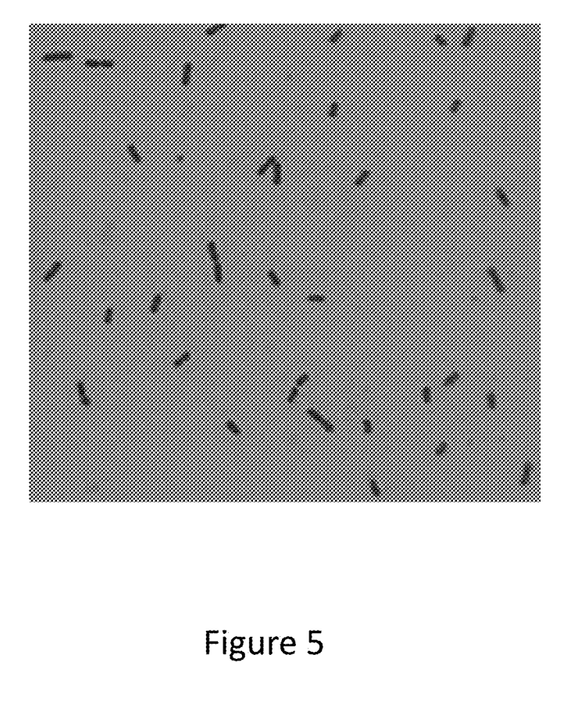
FIG. 5. Cell morphology of *Lactobacillus plantarum* CCFM8610 (1000×).
Figure 6:
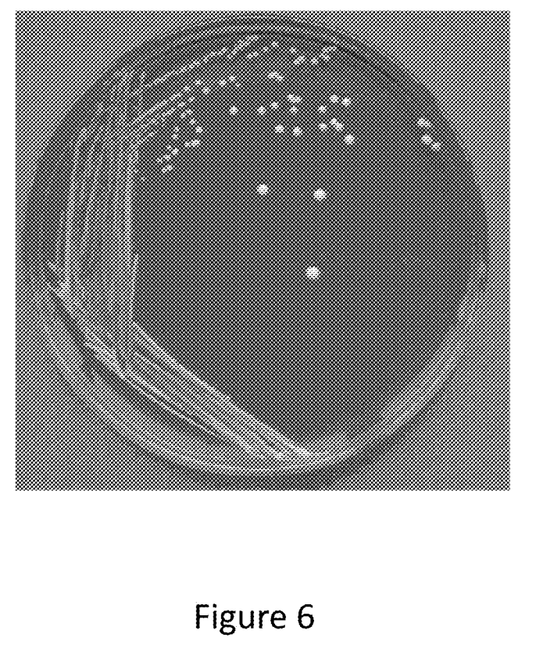
FIG. 6. Colony morphology of *Lactobacillus plantarum* CCFM8610.

*Lactobacillus plantarum* CCFM8610 of the invention has the following characteristics:

Strain morphology: as shown in FIG. 5, *Lactobacillus plantarum* CCFM8610 is a rod-shaped gram-positive bacterium. It is 0.9-1.2 μm wide and 3-8 μm long, has blunt rounded ends and does not form spores. Colony characteristics: *Lactobacillus plantarum* CCFM8610 can form colonies on MRS agar plates without producing pigment. The colony is 0.3-2.3 mm in diameter with a round shape from the front view and a protruding shape from the side view. The colony is ivory and opaque with a moist and smooth surface and a neat edge (see FIG. 6). Growth characteristics: the optimum temperature for cell growth is 30-37° C. The maximum and the minimum growth temperatures are 43° C. and 12° C., respectively. The highest and the lowest initial growth pH values are 9.0 and 2.5, respectively. The optimum initial growth pH is 6.0. *Lactobacillus plantarum* CCFM8610 has a relatively short lag phase of about 4 hours and a logarithmic phase of about 16 hours, after which it reaches the stationary phase.

Preservation methods for *Lactobacillus plantarum* CCFM8610

*Lactobacillus plantarum* CCFM8610 can be preserved in two ways: (1) preserve under −75° C. in suspension with 30% (w/w) glycerol solution as protective solution; (2) preserve in the form of freeze-dried powder under 4° C.

The culture method for *Lactobacillus plantarum* CCFM8610: culture *Lactobacillus plantarum* CCFM8610 in MRS medium at 37° C. for 18-36 hours under anaerobic condition.

2. Application of *Lactobacillus plantarum* CCFM8610 for Preparing Cadmium-Removing Drugs and Fermented Foods.

The cadmium-removing drugs of the invention comprise *Lactobacillus plantarum* CCFM8610 powder and pharmaceutically acceptable drug carriers.

The *Lactobacillus plantarum* CCFM8610 powder can be produced by freeze-drying method or other conventional preparation methods (e.g. spay drying method). The resulting powder contains at least $10^6$ CFU viable *Lactobacillus plantarum* CCFM8610 per gram. The bacteria concentration was measured using standard plate count method well known to those of ordinary skill in the field. The concentration of *Lactobacillus plantarum* CCFM8610 in cadmium-removing drugs is 15-35% (w/w), preferably 18-32% (w/w), and more preferably 20-30% (w/w).

The "pharmaceutically acceptable drug carriers", as used herein, refers to conventional pharmaceutical drug carriers that are commonly used in pharmaceutical drugs. For example, it can be one or more kinds of pharmaceutical grade fillers, adhesives, wetting agents, disintegrants, lubricants and flavoring agents.

A "pharmaceutical filler", as used herein, refers to an excipient or a diluent which is used to help manufacture drug tablets by increasing the weight and the volume of a drug. It also refers to an absorbent, which is used to absorb excess liquid in the raw pharmaceutical material. For example, the fillers can be starch, sucrose, lactose, calcium sulfate or microcrystalline cellulose. Preferably, the pharmaceutical filler is starch, sucrose or microcrystalline cellulose. More preferably, the pharmaceutical filler is starch or microcrystalline cellulose.

A "wetting agent", as used herein, refers to certain liquid which can help pharmaceutical raw material become moist and sticky, and easy to form a particle. For example, the wetting agent can be water, ethanol, starch or syrup. Preferably, the wetting agent is water, ethanol or starch. The amount of wetting agents in the total weight of cadmium-removing drugs is 0.1-3.0% (w/w).

The term "adhesive", as used herein, refers to viscous substance which can help raw drug materials to form granules when the drug materials themselves are non-sticky or have insufficient viscosity. The adhesives, for example, can be cellulose derivatives, alginate, gelatin or polyvinylpyrrolidone. Preferably, the adhesive is cellulose derivatives, gelatin or polyvinyl pyrrolidone. More preferably, the adhesive is gelatin or polyvinylpyrrolidone. The amount of adhesives in the total weight of cadmium-removing drugs is 0.5-5.0% (w/w).

The term "disintegrant", as used herein, refers to a substance that can be added to a drug tablet to facilitate disintegration of the drug into smaller particles in gastrointestinal fluid. It is known that compression increases the hardness of a drug tablet, which makes it disintegrate slowly in gastrointestinal fluid without disintegrants that can facilitate the disintegration. This would result in less effective drugs. For example, the disintegrant can be carboxymethyl starch, hydroxypropyl cellulose, cross-linked carboxymethyl cellulose, agar, calcium carbonate or sodium bicarbonate. Preferably, the disintegrant is carboxymethyl starch, hydroxypropyl cellulose, cross-linked carboxymethyl cellulose, agar or sodium bicarbonate. More preferably, the disintegrant is carboxymethyl starch, hydroxypropyl cellulose, cross-linked carboxymethyl cellulose orsodium bicarbonate. The amount of disintegrants in the total weight of cadmium-removing drugs is 5.0-15.0% (w/w).

The term "lubricant", as used herein, refers to chemical substances that help to improve the flow of the tablet granulation and prevent the adhesion of tablet materials to the mold in the tableting machine. For example, the lubricants can be talc, calcium stearate, magnesium stearete, gum acacia or polyethylene glycol. Preferably, the lubricants are talc, calcium stearate, magnesium stearete or polyethylene glycol. More preferably, the lubricant is talc or calcium stearate. The amount of lubricants in the total weight of cadmium-removing drugs is 0.5-3.0% (w/w).

The term "flavoring agents", as used herein, refers to chemical substances that can be used to mask or improve bad odors and flavors of a drug so that the bitterness or other unpleasant flavors such as strongly spicy or pungent tastes will be imperceptible for patients. The flavoring agents can be selected from, for example, sweeteners (e.g. simple syrup, sugar, lecithin, orange syrup and cherry syrup), aromatics (e.g. lemon, fennel and peppermint), mucilage (e.g. sodium alginate, gum arabic, gelatin, methyl cellulose and sodium carboxymethyl cellulose), and effervescent mixtures such as citric acid, tartaric acid and sodium bicarbonate.

Preferably, the flavoring agents can be selected from sweeteners such as simple syrup, sugar, orange syrup and cherry syrup, aromatics such as lemon and peppermint, mucilage such as sodium alginate, arabic gum, gelatin, and methyl cellulose, and effervescent mixtures such as tartaric acid and sodium bicarbonate.

More preferably, the flavoring agents can be selected from sweeteners such as sugar, orange syrup and cherry syrup, aromatics such as lemon, mucilage such as sodium alginate and gum arabic, and effervescent mixtures such as tartaric acid and sodium bicarbonate. The amount of flavoring agents in the total weight of cadmium-removing drugs is 0.5-2.0% (w/w).

The cadmium-removing drugs of the invention comprising *Lactobacillus plantarum* CCFM8610 and pharmaceutical grade drug carrier can have a variety of formulations such as be granules, capsules, tablets, pills or oral liquid. The type and amount of drug carriers or excipients can be selected according to particular drug formulations, which is easy to determine and obvious to one with ordinary skills in the pharmaceutical art.

The cadmium-removing drugs of the invention in the formation of granules, capsules, tablets, pills or liquid are prepared using the techniques and apparatus known to those of ordinary skills in the pharmaceutical arts.

The dosage, as used herein, refers to a unit dosage of a drug suitable for a single use in a human. A single dosage contains predetermined amount of active drug substance, e.g. *Lactobacillus plantarum* CCFM8610 powder.

The cadmium-removing fermented foods of the invention can be dairy products, soy bean products, fruit products or vegetable products which are prepared by fermentation with *Lactobacillus plantarum* CCFM8610.

The *Lactobacillus plantarum* CCFM8610 used for fermentation is prepared as follows:

A, Preparation of culture medium. The ingredients are (w/w, %): $H_2O$ 87.7, skim milk (enzymatic hydrolysis milk) 10, glucose 0.5, tryptone 1.5, yeast extract 0.3, pH 6.8. Mix all the ingredients as described above and adjust pH to be 6.8. The percentage is calculated based on total weight.

B, Preparation of protective agent. The ingredients are 100 g/L skim milk, 30 mL/L glycerol, 100 g/L maltodextrin, 150 g/L trehalose, and 10 g/L L-glutamate. Dissolve the ingredients above into water to make a protective agent.

C, Lactobacillus plantarum CCFM8610 is inoculated at a 2-4% (w/w) ratio into a sterile culture medium (sterilized under 110-120° C. for 8 to 12 minutes) and cultured at 37° C. for 18 hours. The cultured biomass is washed 2-4 times with phosphate buffer (pH 7.2) and then suspended in the protective agent to $10^{10}$ CFU/mL. The suspension is then incubated at 37° C. for 60 minutes before subject to the conventional freeze-drying procedure. The freeze-dried *Lactobacillus plantarum* CCFM8610 powder is used as the starter culture.

The cadmium-removing dairy products of the invention can be milk, sour cream or cheese.

Milk, as used herein, refers to cow's milk, mare's milk and reconstituted milk. The reconstituted milk is made with 10-15% milk powder and 85-90% softened water. The milk powder is a milk product widely sold in the market.

Sour cream refers to a dairy product made from regular cream by fermentation with certain types of lactic acid bacteria. Sour cream has many advantages compared to regular cream (sweet cream). The flavor of sour cream is stronger than sweet cream, and has higher content of cream. In addition, lactic acid bacteria can inhibit the growth of harmful microorganisms and reduce the risk of microbial contamination after sterilization.

Cheese is a kind of nutritious food made from fermented milk.

The soy bean products can be soy milk, fermented soybean or soybean paste, which are all traditional Chinese foods.

The vegetable products can be cucumbers, carrots, beets, celeries or cabbage products.

Use the following method to make dairy products, soy bean products, and fruit and vegetable products fermented by *Lactobacillus plantarum* CCFM8610.

Typically, during the production process of cadmium-removing dairy products, soy bean products, fruit products or vegetable products, the starter culture of *Lactobacillus plantarum* CCFM8610 is inoculated into raw materials, and cultured under the pressure and temperature suitable for the growth of the bacteria. The metabolites in fermented products makes the final products have certain acidity, good flavor and other desirable features. The fermented products have a longer storage time, higher nutritious value and are easier to be digested.

In summary, *Lactobacillus plantarum* CCFM8610 of the invention has a good acid tolerance, a good cadmium tolerance, and high cadmium binding capacity. Treating cadmium-exposed mice with *Lactobacillus plantarum* CCFM8610 can effectively decrease tissue cadmium accumulation and facilitate fecal cadmium excretion. *Lactobacillus plantarum* CCFM8610 has a great potential in developing pharmaceutical drugs and fermented foods as antidotes for cadmium toxicity.

EXAMPLES

The following examples are provided by way of illustration only, and not by way of limitation.

Example 1

Cadmium Tolerance Capacity of *Lactobacillus plantarum* CCFM8610

The cadmium solution (150 mg/L) was prepared by dissolving 0.3423 g $3CdSO_4 \cdot 8H_2O$ into 1 L water under sterile conditions. MRS culture medium is well known to those with ordinary skill in the art, which contains tryptone, yeast extract, glucose, sodium acetate, citric acid, diammonium glycyrrhizinate, Tween 80, magnesium sulfate and manganese sulfate, pH6.2-6.4. The cadmium-containing MRS medium (150 mg/L cadmium ion) was prepared by dissolving the MRS solid ingredients in cadmium solution (150 mg/L). Use the same method to make MRS culture medium with 50 mg/L and 500 mg/L cadmium ions.

2% (w/w) *Lactobacillus plantarum* CCFM8610 that entered stable phase were inoculated into the cadmium-containing media above and cultured under 37° C. Cell growth is determined by standard plate count at 0, 2, 4, 6, 8, 12, 16, 20, and 24 hours after the start of the culture. The cell growth curve of *Lactobacillus plantarum* CCFM8610 is shown in FIG. 1. As a control, 1 mL *Lactobacillus plantarum* CCFM8610 was cultured in normal MRS medium without cadmium. The growth curve of the control group is also shown in FIG. 1.

As shown in FIG. 1, in three cadmium-containing media, although the cell growth was inhibited by cadmium in the beginning, the grow rate increased rapidly afterwards. At 24 hours of the culture, the concentration of cells in the MRS medium containing 50 mg/L or 150 mg/L cadmium is nearly as high as that in medium without cadmium. Therefore, *Lactobacillus plantarum* CCFM8610 of the invention has a good cadmium tolerance.

Example 2

Cadmium Binding Capacity of *Lactobacillus plantarum* CCFM8610

Nine lactic acid bacteria strains were isolated from the traditional Chinese foods (e.g. pickles and fermented milk wine) based on the acid tolerance selection criterion (e.g. able to grow under pH 3.0). The nine strains were purified and activated in the MRS medium. The activated bacteria were gently shaken until they were evenly distributed in the medium. They were then subjected to centrifugation at 6000 r/min for 15 minutes. The cell pellets were transferred into a cadmium-containing medium (150 mg/L) to a final bacterial concentration of 1 g/L. For the control group, the cells were transferred to deionized water. The cells were incubated at 37° C. for 1 hour. The cells were then centrifuged at 6000 r/min for 20 min, washed with sterile water, and centrifuged again. After the centrifugation, cell pellets were collected and digested in concentrated $HNO_3$, and further digested in a microwave digestion oven for 20 minutes. The cadmium concentration of the digested solution was measured by atomic absorption spectrum analyzer (Spectr AA 220, Varian, USA). The cadmium binding capacity of different strains is shown in FIG. 2.

As shown in FIG. 2, the cadmium binding capacity varies among the nine strains. *Lactobacillus plantarum* CCFM8610 of the invention has the highest biosorption level to cadmium (10.92 mg/g), whereas *Lactobacillus delbrueckii* CCFM8147 has the lowest biosorption level of cadmium (3.22 mg/g), which is much lower than that of *Lactobacillus plantarum* CCFM8610 strain.

Example 3

Determination of Mice Tolerance to *Lactobacillus plantarum* CCFM8610

The freeze-dried *Lactobacillus plantarum* CCFM8610 powder was suspended in skim milk to a final concentration 2.0×109 CFU/mL. The bacteria suspension was administered daily to ten healthy male Kunming mice (body weight: 20 g) via gavage for a week. The mice death rate and weight change was recorded for a week. The results were shown in the Table 1. The results showed that administration of *Lactobacillus plantarum* CCFM8610 at $2.0 \times 10^9$ CFU/mL has no significant effects on mice. The weight of mice increases over the time and no death is observed. The mice have no obvious pathological symptoms.

TABLE 1

The change of mice weight fed with the *Lactobacillus plantarum* CCFM8610 at the concentration of $2.0 \times 10^9$ CFU/mL

| | Time (d) | | | | | | |
|---|---|---|---|---|---|---|---|
| | 1 | 2 | 3 | 4 | 5 | 6 | 7 |
| Weight (g) | 22.3 ± 2.9 | 22.9 ± 1.3 | 23.1 ± 2.2 | 23.2 ± 2.1 | 23.6 ± 0.9 | 24.6 ± 1.1 | 25.0 ± 1.2 |
| Death | — | — | — | — | — | — | — |

Note:
—, no death.

Example 4

Effects of *Lactobacillus plantarum* CCFM8610 on Decreasing the Tissue Cadmium Level of Cadmium-Exposed Mice 60 healthy adult male mice (body weight: 20-25 g) were randomly divided into 3 groups: a negative control group (no cadmium or CCFM8610), a cadmium-only group and a cadmium plus CCFM8610 (therapy group). At the first day of the animal experiment, the mice in the negative control group were administered 0.5 mL drinking water via gavage; the other two groups were both administered 0.5 mL 3.6 mg/L cadmium solution via gavage. At 1 hour after cadmium exposure, the control and cadmium-only group were administered 0.5 mL skim milk, while the therapy group was administered 0.5 mL skim milk with $2.0 \times 10^9$ CFU/mL *Lactobacillus plantarum* CCFM8610 via gavage. At 48 hours after cadmium exposure, all mice were sacrificed. Livers and kidneys were excised, cleaned and digested for cadmium estimation using Atomic absorption spectrophotometry method as described herein. The results were shown in FIG. 3.

Comparing the cadmium levels in livers and kidneys of three groups of mice, the cadmium level in the therapy group (with cadmium and *Lactobacillus plantarum* CCFM8610) was higher than that of the negative control group, but significantly lower than that of the cadmium-only group. Liver and kidney were target organs for cadmium accumulation, which makes them most vulnerable to cadmium accumulation and toxicity. Within one hour of cadmium exposure, gavage administration of *Lactobacillus plantarum* CCFM8610 can significantly reduce cadmium accumulation in liver and kidney ($P<0.05$), proving that *Lactobacillus plantarum* CCFM8610 can reduce cadmium accumulation in vivo. Example 2 has shown that *Lactobacillus plantarum* CCFM8610 has a strong absorption capacity to cadmium. It can quickly bind cadmium ions in the body, thus preventing them from entering blood and other tissue via intestinal absorption.

Example 5

Effects of *Lactobacillus plantarum* CCFM8610 on Facilitating Fecal Excretion of Cadmium in Cadmium-Exposed Mice 60 adult male mice (body weight 20-25 g) were randomly divided into 3 groups: a control group (no cadmium or CCFM8610), a cadmium-only group and a cadmium plus CCFM8610 (therapy group). At the first day of the animal experiment, the mice in the control group were administered 0.5 mL drinking water via gavage; the other two groups were both administered 0.5 mL 3.6 mg/L cadmium solution via gavage. At 1 hour after cadmium exposure, the control and cadmium-only group were administered 0.5 mL skim milk, while the therapy group was administered 0.5 mL skim milk with $2.0 \times 10^9$ CFU/mL *Lactobacillus plantarum* CCFM8610 (made in example 3) via gavage. At 4, 8, 12, 24 and 48 hours after cadmium exposure, fecal samples of each surviving mouse were collected and digested for cadmium determination using the atomic absorption spectrometry method as described herein. The results were shown in FIG. 4.

Fecal cadmium concentrations in the negative control group were too low to be detected, so these data were not included in the figure. Comparing the cadmium contents in the feces of cadmium-only group and the therapy group at different times after cadmium exposure, fecal cadmium levels were significantly increased in the feces of the therapy group at 8, 12 and 24 hours (p<0.05). These results showed that *Lactobacillus plantarum* CCFM8610 can facilitate fecal cadmium removal in animals. Example 2 has shown that *Lactobacillus plantarum* CCFM8610 has a strong binding ability to cadmium ions. Once it enters the body, it can quickly bind cadmium ions and facilitate cadmium removal from the body through fecal excretion.

The above animal experiments demonstrated that *Lactobacillus plantarum* CCFM8610 has the ability to significantly decrease cadmium accumulation in the tissue and facilitate cadmium removal through fecal excretion.

Example 6

Preparation of Dairy Products Containing *Lactobacillus plantarum* CCFM8610

The starter culture containing *Lactobacillus plantarum* CCFM8610, which can be used for making fermented dietary products, was made as follows:

A, Preparation of culture medium. The ingredients are (w/w, %): $H_2O$ 87.7, skim milk (enzymatic hydrolysis milk) 10, glucose 0.5, tryptone 1.5, yeast extract 0.3, pH 6.8. Mix all the ingredients as described above and adjust pH to be 6.8. The percentage is calculated based on total weight. The skim milk, glucose, tryptone, and yeast extract are commercially available on the market.

B, Preparation of protective agent. The ingredients are 100 g/L skim milk, 30 mL/L glycerol, 100 g/L maltodextrin, 150 g/L trehalose, and 10 g/L L-glutamate. Dissolve the ingredients above into water to make a protective agent.

C, 3% (w/w) *Lactobacillus plantarum* CCFM8610 is inoculated into a sterile culture medium (sterilized under 110-120° C. for 8 to 12 minutes) and cultured at 37° C. for 18 hours. The cultured biomass is washed 3 times with phosphate buffer (pH 7.2) and then suspended in the protective agent to $10^{10}$ CFU/mL. The suspension is then incubated at 37° C. for 60 minutes before subjected to the conventional freeze-drying procedure. The freeze-dried *Lactobacillus plantarum* CCFM8610 powder is used as the starter culture.

D, Preparation of dairy products with *Lactobacillus plantarum* CCFM8610. The skim milk is sterilized at 95° C. for 20 minutes, and cooled down to 4° C. The *Lactobacillus plantarum* CCFM8610 powder (the starter culture prepared above) is added to the skim milk to a final concentration of $10^6$ CFU/mL, and the final dairy product is preserved at 4° C.

Example 7

Preparation of Soy Milk Containing *Lactobacillus plantarum* CCFM8610

The soybeans are soaked in soft water and kept at 80° C. for 2 hours to remove soybean hulls. Drain away the soaking water and grind the soybean in boiling water. The soybean grinding mixture is incubated at 80° C. for 12 min and the resulting slurry is filtered by a 150 mesh sieve. The resulting solution is centrifuged to get crude soy milk. The crude soy milk is heated to 140-150° C., and quickly transferred to and evacuated in a vacuum cooling chamber. Unpleasant flavors in crude soy milk are then quickly removed along with the water vapor. After the degassing, the soy milk is cooled down to 37° C. The freeze-dried *Lactobacillus plantarum* CCFM8610 powder is then added into the soy milk to reach a final concentration of $10^6$ CFU/mL. The final soy milk containing *Lactobacillus plantarum* CCFM8610 is preserved at 4° C.

Example 8

Preparation of Fruit and Vegetable Juice Containing *Lactobacillus plantarum* CCFM8610

Juice squeezed out of fresh vegetables or fruits is heat sterilized at 140° C. for 2 seconds and quickly cooled down to 37° C. The freeze-dried *Lactobacillus plantarum* CCFM8610 powder is then added to the sterilized juice to reach a concentration of $10^6$ CFU/mL. The juice containing *Lactobacillus plantarum* CCFM8610 is preserved at 4° C.

Example 9

Preparation of Capsules Containing *Lactobacillus plantarum* CCFM8610

*Lactobacillus plantarum* CCFM8610 is cultured with MRS medium for 24 hours and the bacteria cells are harvested by centrifugation at 4000 r/min, 4° C. for 20 min. *Lactobacillus plantarum* CCFM8610 cells are washed twice with phosphate buffer (pH 7.2) and suspended in skim milk to a final concentration of $2 \times 10^{10}$ CFU/mL. The cell suspension is dispersed in sodium alginate solution (3%, w/w) uniformly by stifling. The resulting mixture is extruded to calcium chloride solution (2%, w/w) to form particles. Wait 30 minutes for particle formation and collect the particles by filtration. The particles are then freeze-dried to generate powders which can be encapsulated to get the end products, capsules with viable *Lactobacillus plantarum* CCFM8610.

Example 10

Preparation of Starter Cultures Containing *Lactobacillus plantarum* CCFM8610

Starter cultures containing *Lactobacillus plantarum* CCFM8610 was made using the following method:
  Culture medium (w/w, %): $H_2O$ 87.7, skim milk (enzymatic hydrolysis) 10, glucose 0.5, tryptone 1.5, yeast extract 0.3, pH 6.8.
  Protective agent: 100 g/L skim milk, 30 mL/L glycerol, 100 g/L maltodextrin, 150 g/L trehalose, 10 g/L L-glutamate, dissolvent $H_2O$.
  3% (w/w) *Lactobacillus plantarum* CCFM8610 was inoculated into sterile culture medium (sterilized at 115° C. for 10 minutes) and cultured at 37° C. for 18 hours. The bacteria cells were washed 2 times with phosphate buffer (pH 7.2) and suspended in the protective agent to a final concentration of $10^{10}$ CFU/mL. The suspension was then incubated at 37° C. for 60 min and was made into a dry powder using a conventional freeze-drying procedure. The freeze-dried *Lactobacillus plantarum* CCFM8610 powder can be used as a starter culture to produce fermented dairy products, soy bean products and fruit/vegetable products.

Example 11

Preparation of Fermented Milk Using *Lactobacillus plantarum* CCFM8610

Sugar is dissolved in fresh milk and the milk is homogenized under 65° C. and 20 MPa. It is then sterilized under 95° C. for 5 minutes. After that, the temperature is cooled down to 35° C. Mix dry powders of three different bacteria strains, *Lactobacillus plantarum* CCFM8610 of the invention, commercially available *Lactobacillus bulgaricus*, and commercially available *Streptococcus thermophilus*, at a mass ratio of 1:1:1. The bacteria mixture is inoculated at a weight ratio of 0.3% to the sterilized fresh milk, mixed until evenly distributed, and fermented at 35° C. to produce milk curds. The resulting curds are kept refrigerated at 4° C. for 24 hours to obtain the final fermented milk products.

Example 12

Preparation of *Lactobacillus plantarum* CCFM8610 Tablet

Ingredients (%, w/w): *Lactobacillus plantarum* CCFM8610 powder (prepared in Example 10) 25.7, starch 55.0, cellulose derivatives 4.5, sodium carboxymethyl starch 12, talcum powder 0.8, sugar 1.0 and $H_2O$ 1.0.

Mix the above ingredients to generate wet tablets using conventional methods known to those of ordinary skills in the pharmaceutical arts. The wet tablets are compressed into tablets using a drug compression machine (made by Zhongnan Pharmaceutical Machinery, Changsha, Hunan, China), dried by a small drug drying machine (made by Qingzhou City Yikang Chinese Traditional Medicine Co., Ltd, Qingzhou, Shandong, China) and packed into tablets of *Lactobacillus plantarum* CCFM8610.

While the present invention has been described in some details for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A cadmium-removing bacterial product, comprising at least $10^6$ CFU/g viable *Lactobacillus plantarum* CCFM8610 and a protective agent comprising glycerol, wherein said *Lactobacillus plantarum* CCFM8610 was deposited in China General Microbiological Culture Collection Center (CGMCC), Institute of Microbiology of Chinese Academy of Sciences, No. 1 Beichen West Road, Chaoyang District, Beijing, China, on May 3, 2012 with the accession number of CGMCC No. 6077, and wherein said protective agent stabilizes said *Lactobacillus plantarum* CCFM8610 during cold temperature preservation or processing.

2. The cadmium-removing bacterial product of claim 1, wherein said *Lactobacillus plantarum* CCFM8610 has the following characteristics:

(1) good acid tolerance with the ability to grow well under pH 3.0 to 9.0 and survive under pH 2.5;
(2) good tolerance to cadmium when cultured in a cadmium-containing culture medium;
(3) good cadmium binding capacity when incubated in a cadmium-containing aqueous solution; and
(4) ability to effectively decrease tissue cadmium accumulation and facilitate fecal excretion of cadmium in cadmium-exposed mice.

3. The cadmium-removing bacterial product of claim 1, wherein said cadmium-removing bacterial product comprises *Lactobacillus plantarum* CCFM8610 suspended in glycerol solution.

4. The cadmium-removing bacterial product of claim 1, wherein said protective agent further comprises maltodextrin, trehalose, or L-glutamate.

5. The cadmium-removing bacterial product of claim 1, wherein said cadmium-removing bacterial product is a bacterial powder comprising the viable *Lactobacillus plantarum* CCFM8610, glycerol, maltodextrin, trehalose, and L-glutamate.

6. A cadmium-removing pharmaceutical drug, comprising the cadmium-removing bacterial product of claim 1 and pharmaceutically acceptable drug carriers.

7. The cadmium-removing pharmaceutical drug of claim 6, wherein said cadmium-removing pharmaceutical drug comprises 15-35% (w/w) of said cadmium-removing bacterial product, wherein said cadmium-removing bacterial product contains at least $10^6$ CFU/g *Lactobacillus plantarum* CCFM8610.

8. The cadmium-removing pharmaceutical drug of claim 6, wherein said pharmaceutically acceptable drug carriers is selected from the group consisting of pharmaceutical grade fillers, adhesives, wetting agents, disintegrants, lubricants and flavoring agents.

9. The cadmium-removing bacterial product of claim 1, wherein said cadmium-removing bacterial product is a food product.

10. The cadmium-removing bacterial product of claim 9, wherein said cadmium- removing food products comprise dairy products, soy bean products, fruit or vegetable products.

11. The cadmium-removing bacterial product of claim 10, wherein said dairy product is selected from milk, sour cream and cheese; wherein said soy bean product is selected from soy milk, salted black beans and soybean paste; and wherein said fruit and vegetable product is selected from cucumbers, carrots, beets, celeries and cabbage products.

* * * * *